United States Patent [19]

Kemp

[11] Patent Number: 4,636,221
[45] Date of Patent: Jan. 13, 1987

[54] ELBOW LOCK MECHANISM

[75] Inventor: Martin Kemp, Aldershot, England

[73] Assignee: Hugh Steeper Limited, London, England

[21] Appl. No.: 710,917

[22] Filed: Mar. 12, 1985

[30] Foreign Application Priority Data

Mar. 16, 1984 [GB] United Kingdom ............... 8406928

[51] Int. Cl.$^4$ ............................................. A61F 2/54
[52] U.S. Cl. ................................................. 623/59
[58] Field of Search .................. 623/59, 57, 60, 24, 623/25, 26; 74/813 L; 901/14

[56] References Cited

U.S. PATENT DOCUMENTS 3,545,628 12/1970 Dechantsreiter ............... 74/813 L
3,833,942 9/1974 Collins ................................. 623/60

Primary Examiner—Richard J. Apley
Assistant Examiner—James Prizant
Attorney, Agent, or Firm—Kinzer, Plyer, Dorn & McEachran

[57] ABSTRACT

The invention concerns an elbow lock mechanism for use in artificial arms, comprising a locking bolt which is mounted for axial movement on a carriage which is movable by electric drive means between two positions, there being a spring on the carriage which urges the bolt into its locking position when the carriage is in one position and which urges the bolt into an unlocking position when the carriage is in the other position.

5 Claims, 9 Drawing Figures

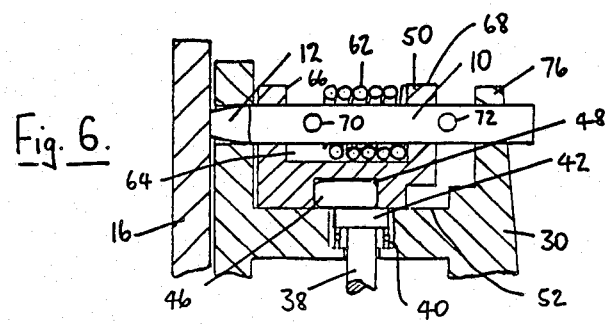

ELBOW LOCK MECHANISM

This invention relates to elbow lock mechanisms for use in artificial arms, the term "artificial arm" being used herein in a broad sense to cover not only the artificial arms or prosthesis worn by those with a missing limb but also the mechanical arms provided on robots and other automatic equipment used in industry.

It is already known to provide electrically-powered lock mechanisms in the elbow portions of artificial arms. In one such construction an electrically-driven bolt is used to lock the elbow in a selected position, but this has the disadvantage that the electric motor serving to move the bolt may be kept energised for much longer than is necessary while the person wearing the artificial arm brings the elbow into a desired angular position.

In another form of elbow lock mechanism, flexion of the arm is achieved by electric power means while movement of a locking bolt to lock the elbow in a chosen position is effected by a hair spring. This is an improvement over the other prior construction described above, but it has the disadvantage that the spring acts only in one direction, namely, to drive the bolt into its locking position. In particular, the force of the spring cannot be used to hold the bolt in an "unlocked" position.

The aim of the present invention is to provide an elbow lock mechanism which overcomes the above-mentioned disadvantages, and according to the invention an elbow locking mechanism comprises a locking bolt or pin which is mounted for axial movement on a carriage which is movable by electric drive means between two positions, there being a spring on the carriage which urges the bolt or pin into its locking position when the carriage is in one position and which urges the bolt or pin into an unlocking position when the carriage is in the other position.

An example of an elbow lock mechanism in accordance with the invention is shown in the accompanying drawings, in which:

FIGS. 6–9 are four views of a particular portion of FIG. 2 showing components thereof in different relative positions.

Figure 1:
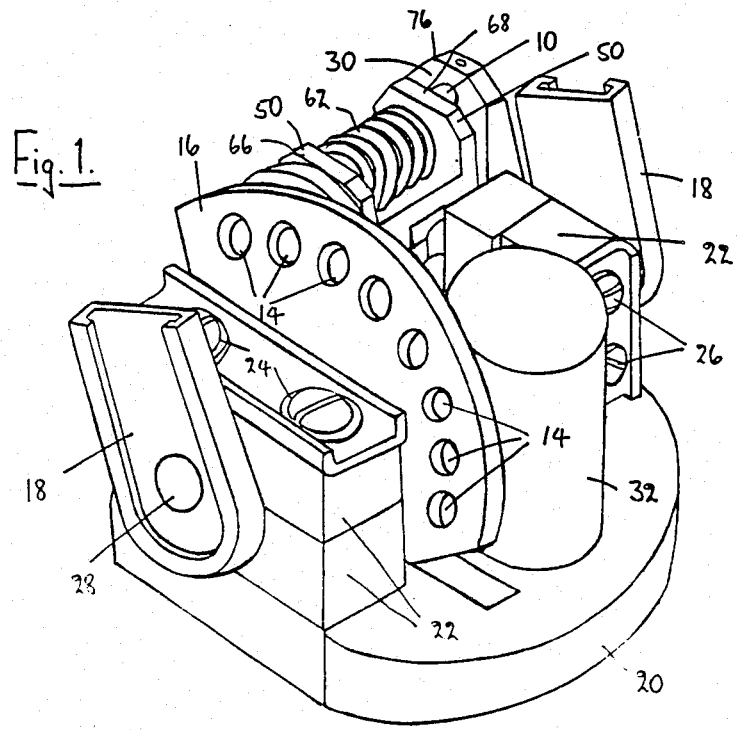
FIG. 1 is a perspective view of the mechanism.
Figure 2:
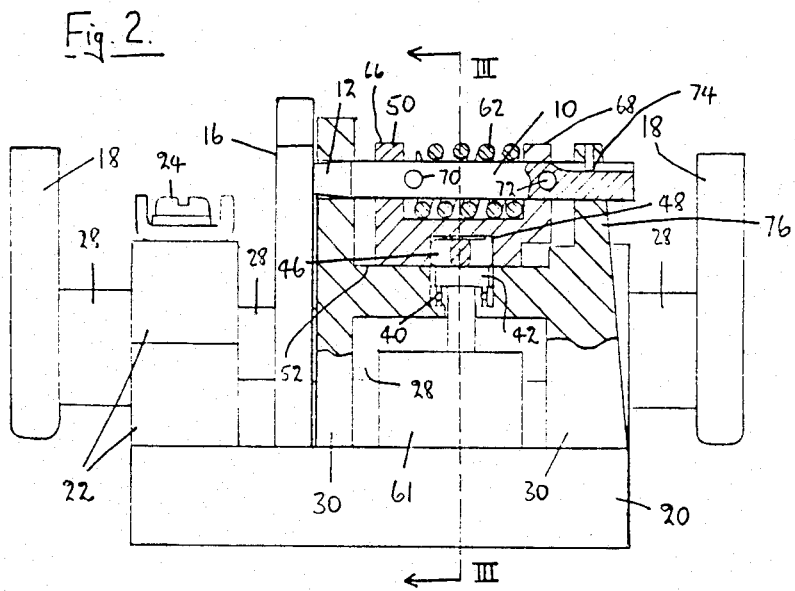
FIG. 2 is a part-sectional front view of the mechanism.

The elbow lock mechanism shown in the drawings comprises an axially-movable locking pin or bolt 10 the tapered nose 12 of which is adapted to enter any selected one of a number of holes 14 arranged in an arc on a quadrant plate 16 so as to lock the elbow mechanism against movement of the twin-members 18 with respect to a base member 20 and a shaft mounting 22 bolted thereon by means of bolts 24 and 26. The twin members 18 form part of the lower arm or limb of a prosthesis, while the base member 20 is connected by appropriate means to the upper arm or limb of the prosthesis. To permit angular movement of the elbow joint thus formed, the twin members 18 are carried on the ends of a rotatable pivot shaft 28 which passes through the quadrant plate 16, the shaft and the quadrant being fast with each other. The shaft 28 is supported by the shaft mounting 22.

Figure 3:
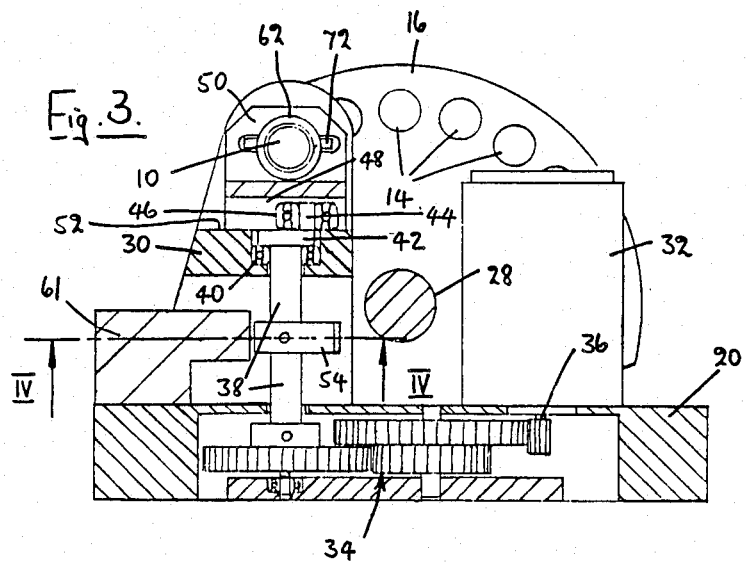
FIG. 3 is a section taken on the line III—III in FIG. 2.

The base member 20 further supports, on its upper surface, a bracket 30 and an electric drive motor 32. Part of the base member 20 is hollow (see FIG. 3) so as to house a reduction gear 34 between the shaft 36 of the motor and an upright driven shaft 38. The upper end of the driven shaft 38 is rotatably supported in a bearing 40 and is capped by a disc 42 having a crank-pin 44 (see FIG. 3) carrying a roller 46. The roller 46 is received snugly within a transverse recess 48 in a carriage 50 arranged for sliding movement on a horizontal surface 52 on the bracket 30. It thus follows that rotation of the drive shaft 38 causes the carriage 50 to slide over the surface 52 in a direction parallel to the locking pin 10.

Figure 4:
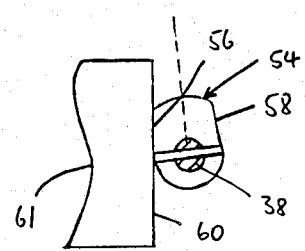
FIG. 4 is a section taken on the line IV—IV in FIG. 3.
Figure 5:
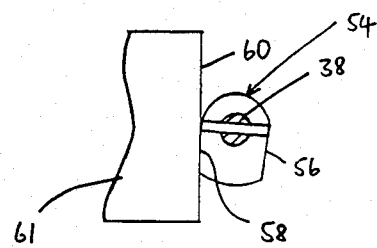
FIG. 5 is a view similar to FIG. 4 with a component thereof in a different position.

In order to restrict movement of the carriage 50, a stop-cam 54 is mounted fast on an intermediate portion of the upright drive shaft 38. As shown in FIGS. 4 and 5, the stop-cam 54 has two "flats" 56 and 58 on its peripherial surface which abut against a stop surface 60 on a bracket 61 at the two extreme positions of the carriage 50.

Surrounding the central position of the locking pin 10 with radial clearance is a helical compression spring 62 supported by the carriage 50 in an upper recess 64 formed by two separately-extending projections 66 and 68 on the carriage. Two laterally-projecting stubs or stub-shafts 70 and 72 on the locking pin are adapted to engage respective ends of the spring 62 at appropriate times as will be explained below. Rotation of the locking pin 10 about its axis is prevented by a pin-and-slot connection 74 between the pin and an upper portion 76 of the bracket 30.

The elbow lock mechanism described above operates in the following way:

The electric motor 32 of the mechanism is activated by a myoelectric or other electrical signal from, say, a microswitch. At this stage the locking mechanism is completely disengaged with the pin 10 and the carriage 50 in the positions shown in FIG. 9. The motor, driving via the reduction gear 34 and the crank-pin assembly 44,46, moves the carriage 50 to the position shown in FIG. 6 whereby the spring 62 is compressed between the projection 68 on the carriage and the stub-shaft 70 on the pin 10. Accordingly, the locking pin 10 is acted on by the spring rather then the carriage so that, should there be no quadrant hole 14 aligned with the locking pin, the spring will be compressed to the maximum extent as the carriage completes its cycle. The stop-cam 54 is arranged to allow the crank-pin 44 to run over-centre, thus preventing the compressed spring from driving the carriage back. This enables the motor to be switched off when the stop position is reached to prevent further current drain. The motor is switched off by an electronic drive circuit (not shown) which senses the motor stall condition.

The spring 62 continues to exert a force upon the locking pin 10 until either the wearer moves the quadrant 16 so that the pin 10 enters one of the holes 14 and the elbow locks as shown in FIG. 7, or another control signal to the motor drives the carriage to the unlock position shown in FIG. 8. In this unlock position the locking pin may be prevented from moving by an excessive movement applied to the quadrant 16, causing a frictional force on the locking pin which is greater than the spring force. Once this frictional force is removed, however, the compressed spring 62 shown in FIG. 8 will act on the stub-shaft 72 on the pin 10 to dis-engage the nose 12 of the pin 10 from the hole 14 in which it has been inserted.

The above-described elbow lock mechanism has a number of advantages as follows:

1. The electrical consumption of the motor 32 is reduced by storing the actuating force for the pin 10 in the spring 62. Typically a patient may take 1 or 2 seconds to align the quadrant 16 compared with 1/10 second for the motor to drive the carriage 50 against the spring. 2. The force applied to the locking pin 10 for engagement and disengagement is independent of the motor 32 and state of charge of the battery, being dependent only on the stiffness of the spring 62. This is particularly important in the case of disengagement where it is possible to choose a value of spring which prevents an inadvertent disengagement signal from causing an actual disengagement when a heavy load is being carried. Disengagement will only occur when the wearer supports the load and so relieves the movement acting on the locking pin 10. 3. The drive system is isolated from shock loadings applied to the locking mechanism and may therefore be made lighter.

The elbow lock mechanism can be used for patients who have difficultly operating existing mechanical lock mechanisms. In addition, the powered lock facilitates usage in conjunction with a servo-controlled hand controlled by a back strap, as this can also be used for elbow flexion. If a microswitch or other sensing element is operated by the locking pin, then the power to the hand may be switched off during elbow flexion and back on when the elbow locks, thereby obviating any interaction in the use of the back strap.

I claim:

1. An elbow lock mechanism for use in artificial arms, comprising a carriage support and a carriage movable thereon between a first position and a second position, electric drive means including an electric motor and a shaft rotatably supported in a bearing, a disc capping the shaft, a crank-pin on the disc and a roller on the crank-pin, a transverse recess in the carriage arranged to receive the roller in a snug fashion so that rotation of the shaft by the electric motor causes the carriage to move on the carriage support, a locking bolt mounted for axial movement on the carriage to enter and withdraw from a locking aperture in a bolt-receiving member, and a spring on the carriage to urge the bolt into locking engagement with the bolt-receiving member when the carriage is in the first position and to urge the bolt into a disengaged position with respect to the bolt-receiving member when the carriage is in the second position, the movement of the carriage on the carriage support being in a direction substantially parallel to the longitudinal axis of the locking bolt.

2. An elbow lock mechanism as claimed in claim 1, wherein a stop-cam is mounted fast on an intermediate portion of the shaft in order to restrict movement of the carriage on the carriage support, the stop-cam being provided with two flat portions on its peripheral surface which abut against a stop surface on a bracket at the first and second positions of the carriage.

3. An elbow lock mechanism as claimed in claim 1, comprising a base member which supports a bracket serving as the carriage support, at least part of the base member being hollow so as to house a reduction gear between a drive shaft of the motor and the shaft capped by the disc.

4. An elbow lock mechanism for use in artificial arms, comprising a carriage support and a carriage movable thereon between a first position and a second position, electric drive means including an electric motor and a shaft operably connected to the carriage to move the carriage on the carriage support, a locking bolt mounted for axial movement on the carriage to enter and withdraw from one of a plurality of locking apertures arranged in an arc on a quadrant plate serving as a bolt-receiving member, a spring on the carriage to urge the bolt into locking engagement with the bolt-receiving member when the carriage is in the first position and to urge the bolt into a disengaged position with respect to the bolt-receiving member when the carriage is in the second position, two laterally-projecting stubs on the locking bolt adapted to engage respective ends of the spring as the carriage moves on the carriage support with rotation of the locking bolt about its axis being prevented by a pin-and-slot connection between the bolt and a portion of the carriage support, and a stop member mounted fast on an intermediate portion of the shaft in order to restrict movement of the carriage on the carriage support.

5. An elbow lock mechanism as claimed in claim 4, wherein the spring on the carriage is a helical compression spring which surrounds the central portion of the locking bolt with radial clearance, the spring being located in a recess formed by two spaced-apart projections on the carriage.

* * * * *